United States Patent

McCardell et al.

[11] 3,976,369
[45] Aug. 24, 1976

[54] ALPHA METER ATTACHMENT FOR UNDERWATER OPTICAL SYSTEMS

[75] Inventors: Peter D. McCardell, San Diego; Paul J. Heckman, Jr., Rancho Santa Fe, both of Calif.

[73] Assignee: The United States of America as represented by the Secretary of the Navy, Washington, D.C.

[22] Filed: Feb. 27, 1975

[21] Appl. No.: 553,698

[52] U.S. Cl. .................................. 350/319; 356/208
[51] Int. Cl.² ........................................ G02B 5/00
[58] Field of Search ............ 250/573, 574; 350/319; 356/201, 207, 208

[56] References Cited
UNITED STATES PATENTS
3,885,162  5/1975  Geertz .................. 250/573 X

OTHER PUBLICATIONS

Jenkins et al., *Fundamentals of Optics*, second ed., McGraw-Hill, p. 489, 1950.

*Primary Examiner*—John K. Corbin
*Assistant Examiner*—Matthew W. Koren
*Attorney, Agent, or Firm*—Richard S. Sciascia; Ervin F. Johnston; William T. Skeer

[57] ABSTRACT

An improved viewing port for underwater oceanographic vehicle provides for establishing a standard length optical test path in the underwater environment with no modifications or additional passages through the hull of the vehicle.

10 Claims, 5 Drawing Figures

ALPHA METER ATTACHMENT FOR UNDERWATER OPTICAL SYSTEMS

STATEMENT OF GOVERNMENT INTEREST

The invention described herein may be manufactured and used by or for the Government of the United States of America for governmental purposes without the payment of any royalties thereon or therefor.

FIELD OF THE INVENTION

This invention pertains to the fields of oceanographic instrumentation and marine engineering. More particularly, this invention pertains to improvements in oceanographic submersibles. In still greater particularity, this invention pertains to improved structure to permit optical measurements in the underwater environment. By way of further characterization, the invention pertains to an improved port for use in oceanographics submersible. In still greater particularity, but without limitation thereto, the invention pertains to the provision of a novel prism and port construction to establish a standard length optical path in the underwater medium.

DESCRIPTION OF THE PRIOR ART

As man's exploration of his underwater environment continues, a greater variety of scientific measurements and data is continuously needed in the pursuit of a complete understanding of this important region. Such measurements frequently include optical measurements. Photometric data is also obtained which is useful in interpreting the optical measurements and photographic records made from the oceanographic submersible.

Prior art constructions to make various photometric measurements in the vicinity of submersible vehicles have required the mounting of optical elements at an extended distance from the submersible to establish a datum path. This structure establishing a datum path frequently interferes with maneuvering and positioning the vehicle close to the desired investigative area. That is, structures extending outwardly into the underwater environment from an oceanographic submersible are prone to become entangled in underwater marine growths and to interfere with the free movement of the manipulators carried by the vehicle. Also this equipment required separate ports or hull penetrating structure.

SUMMARY OF THE INVENTION

This invention provides an optical path using multiple light transmissions between two especially configured reflectors carried on the exterior surface of an optical port. This construction obviates the need for structure extending outwardly from the oceanographic submersible and, additionally, permits cooperating equipment of several types to be used in conjunction with a single optical datum path. Further, the port used for support of the reflectors may be used as a general purpose viewport.

STATEMENT OF THE OBJECTS OF INVENTION

It is accordingly an object of this invention to provide a viewing port for an oceanographic submersible.

A further object of this invention is to provide a viewing port from oceanographic submersible having optical structure carried thereon to establish a datum test path.

A still further object of this invention is to provide a viewing port for an oceanographic submersible including optical reflector carried thereby.

A still further object of this invention is to provide an improved viewing port for an oceanographic submersible having an optical datum path thereon established by a plurality of reflecting prisms.

DESCRIPTION OF THE PREFERRED EMBODIMENTS

Figure 1:
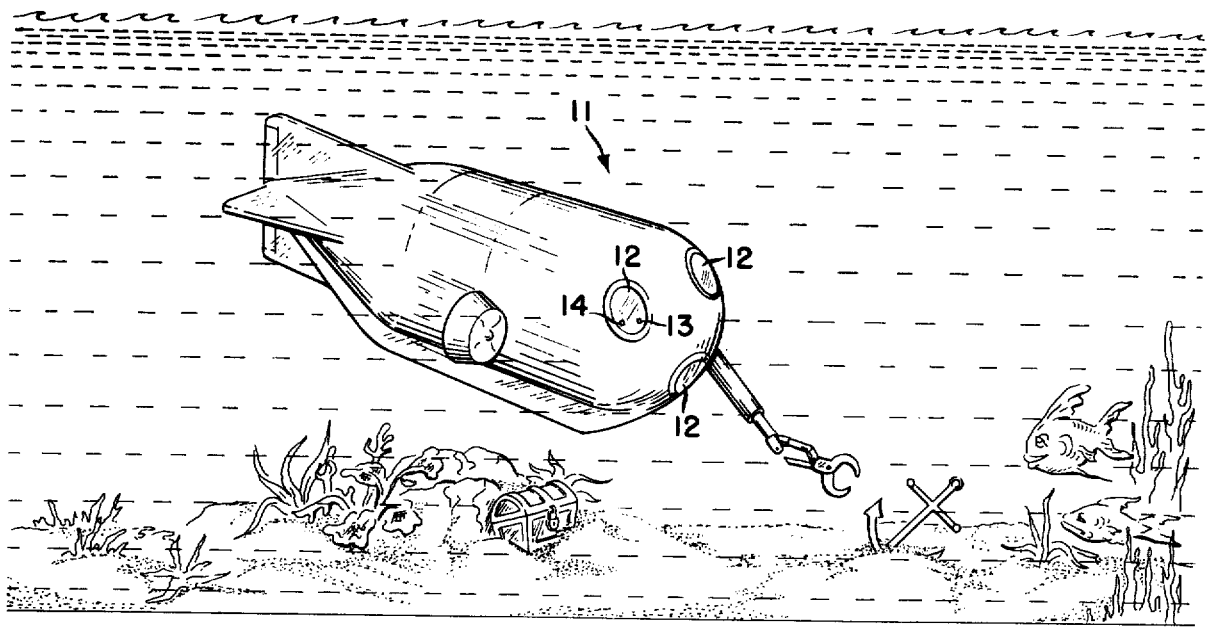
FIG. 1 is a perspective view of an oceanographic submersible employing the viewing port of the invention.

Referring to FIG. 1, an oceanographic submersible is indicated generally at 11 operating beneath the surface of a body of water. A plurality of viewing ports 12 are located in the forward end of oceanographic submersible 11 and permit visual inspection of the underwater environment from within oceanographic vehicle 11 or oceanographic measurements employing optics to be made from within oceanographic submersible vehicle 11. Mounted on the exterior of viewing port 12 is an entry-reentry reflector 13. Also mounted on viewing port 12 is a retroreflector 14.

Figure 2:
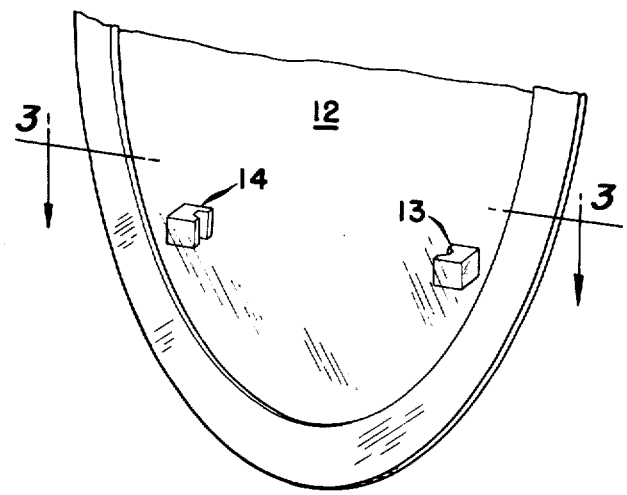
FIG. 2 is a perspective view of the viewing port according to the invention.

Referring to FIG. 2, the location and general configuration of entry-reentry reflector 13 and retroreflector 14 becomes more apparent. Thus, it may be seen that retroreflector 14 is positioned in optical alignment with entry-reentry reflector 13.

Figure 3:
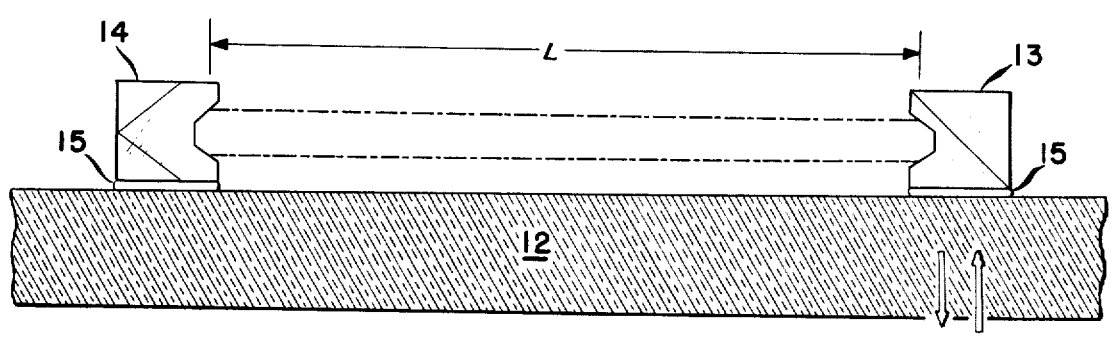
FIG. 3 is a sectional view of the viewing port according to the invention taken along lines 3—3 of FIG. 2.

Referring to FIG. 3, a sectional view of viewing port 12 illustrates that entry-reentry reflector 13 and retroreflector 14 are attached to viewing port 12 by means of a cementuous bond 15.

It should be noted, viewing port 12 is illustrated as a discontinuous unit. That is, the marginal portions thereof are not illustrated. It should be apparent that the marginal portions of viewing port 12 may be of conventional undersea viewing port construction practice. That is, it may employ conical or radiused marginal portions to fit within a conventional hull penetrating cell. Likewise, viewing port 12 may be thicker relative to its diameter than illustrated in FIG. 3. Since such constructional variations are well known and understood in the marine engineering arts, further description thereof is deemed unwarranted for the understanding of the instant invention.

FIG. 3 also illustrates an advantage of the instant system over the prior art in that the same optical datum path may be used with a variety of instruments. That is, the interior of submersible vessel 11 may contain a mounting which positions various optical instruments in cooperation with reflectors 13 and 14 on the exterior of part 12 to establish an external optical transmission path through the seawater. Thus, a transmissometer is shown in operative relation with entry-reentry reflector 13 as indicated by the hollow arrows entering and exiting viewing port 12. Of course, other instruments may be similarly positioned. Since the particular details of the optical test instrument are not an essential part of the instant invention, they need not be described in greater detail for the complete understanding of the invention.

As shown in FIG. 3, the entry-reentry reflector 13 is positioned at a predetermined distance, L, from retroreflector 14. As will become more apparent, this establishes an optical datum path of twice the dimension of the indicated path L. This optical path is illustrated by the broken line on FIG. 3. If desired, retroreflector 14 may be mounted on the exterior surface of oceanographic submersible vehicle 11 instead of being mounted on viewing port 12. This alternative mounting while providing a greater length of optical test path has the disadvantage of requiring more precise optical alignment when replacing or surfacing viewing port 12. Because of recent advances in photoelectronics, the additional length is not required, and therefore the mounting on viewing port 12 is to be preferred.

Figure 4:
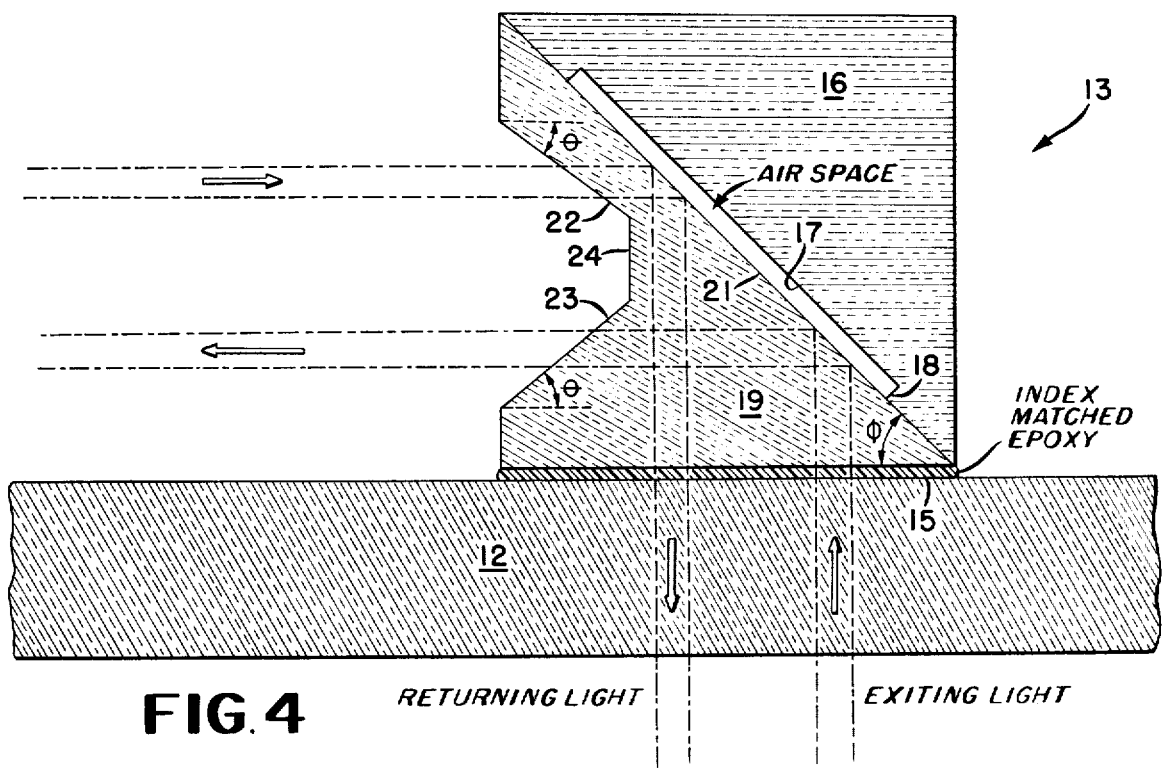
FIG. 4 is a sectional view of the entry-reentry reflector shown in FIG. 3.

Referring to FIG. 4, the details of entry-reentry reflector 13 are illustrated. Entry-reentry reflector 13 is composed of a two part prism including portions 16 and 19. Prism portions 16 and 19 are joined with a conventional optical cementing technique and have satisfactorily withstood the arduous operating conditions imposed upon the system. It should also be noted at this point that entry-reentry reflector 13 is joined to viewing port 12 by means of an index matched epoxy cement. That is, an epoxy cement having an optical index of refraction corresponding to that of inner prism 19 and viewing port 12 is employed for this purpose.

Outer prism 16 is figured to have an air space at the junction of prisms 16 and 19 by recessing a face 17 by means of a depressed wall 18. Of course, the relative dimensions of the air space are exaggerated and in practice wall 18 may be of small dimensions, less than one millimeter. The purpose of the air space confined between outer prism 16 and inner prism 19 is to establish an air interface adjacent prism 19. The junction angle $\phi$ is chosen such that a critical angle is obtained between inner prism 19 and the enclosed air space and to assure a reflection parallel to port 12. This critical angle is a well understood optical construction providing total internal reflection between two bodies having different indices of refraction. This choice of reflection angle $\phi$ causes the light exiting submersible vehicle 11 to be reflected at right angles to its transmission direction and exit prism 19. The exit face 23 of interior prism 19 is ground at an angle $\theta$ with respect to the exterior face thereof to provide an optical path free of reflection. This angle, known as Brewster's Angle, is well understood in the optical arts and may be readily calculated from the index refraction of inner prism 19 and the ambient seawater.

Similarly, entrance face 22 is also disposed at Brewster's Angle with respect to the exterior surface.

Rather than having exit faces 22 and 23 meet to form a line junction, a parallel face 24 truncates or intercepts the figure of faces 22 and 23 to provide for an all glass internal transmission path as illustrated.

Figure 5:
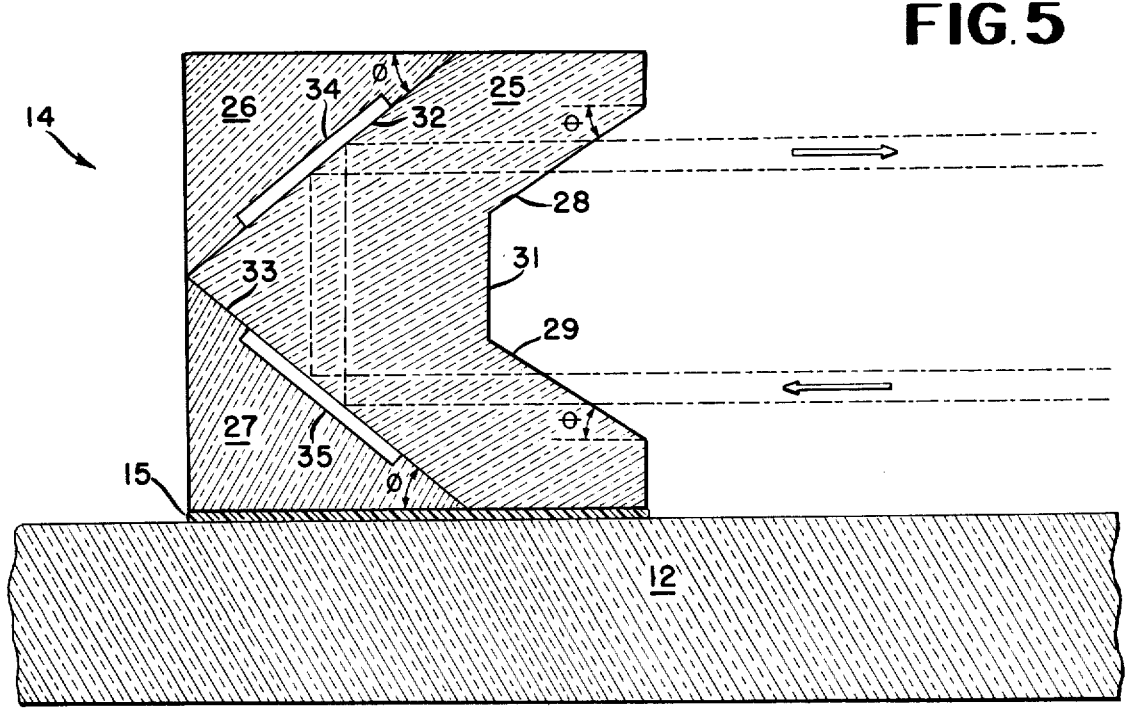
FIG. 5 is a sectional view of the retroreflector prism shown in FIG. 3.

Referring to FIG. 5, the constructional details of retroreflector 14 are illustrated. As the name implies, retroreflector 14 returns light exiting entry-reentry prism 13 to the prism in a parallel and slightly displaced path. The particular construction accomplishing this retroreflection is similar to that used in the entry-reentry prism 13 with the exception that the construction of a captive internal air space is doubled. That is, retroreflector 14 comprises a compound prism 25 which cooperates with two external prisms 26 and 27 to place two air spaces in operative position with the light beam at the critical angles. Thus, the reflecting face 32 of prism 25 has an adjacent air space defined by depressed face 34 of prism 26. Similarly, reflecting face 33 is cooperatively disposed at a critical angle with an air space defined by recessed face 35 of prism 27. Prisms 25, 26 and 27 are, naturally, cemented together to form a unitary assembly in the same fashion that entry-reentry prism 13 was fabricated.

Likewise, entry face 29 of prism 25 is disposed at Brewster's Angle such as to avoid reflection at this interface and exit face 28 is similarly disposed. Entry face 29 and exit face 28 are connected by a face 31 parallel to the external face of retroreflector 14.

It should be clear from the foregoing illustrations and discussion that entry-reentry reflector 13 together with retroreflector 14 provide the required two-way transmission of light therebetween to establish an optical datum path in seawater of twice the separation length. Thus, the internal optical instrument is positioned such that the exiting light is reflected from prism 13 and traverses the distance to retroreflector 14 where it is internally reflected and returned to entry-reentry prism 13 by means of a closely spaced parallel path. Upon impinging entry-reentry reflector 13 this light is returned to the interior of oceanographic submersible 11 where it may be utilized by the optical instrument. Of course, the portions of the optical path occurring within oceanographic vehicle 11 and within the glass portions of viewing port 12 and prism 19 and 25 are a constant and may be easily accommodated by appropriate calibration of the optical instrument.

It will be obvious to those versed in the optical arts that the dimensions of the entry-reentry prism 13 and retroreflector prism 14 may be quite small and yet establish the plural transmission paths. Although the specific dimensions are a matter of choice, the dimensions on the two prisms must be chosen to be such as to position faces 22 and 23 and 28 and 29 in a position equal distant from the external surface of viewing port 12.

Other variations of this construction will suggest themselves to those versed in the optical arts such as to provide greater or fewer transmissions through the separation path. For example, a retroreflector prism identical to retroreflector prism 14 may be cemented to entry-reentry prism 13 on the outer surface thereof and facing in the same direction and another retroreflector prism 14 may be constructed having the dimensions of the combination retroreflector and entry-reentry prism such that a four way transmission is obtained.

The foregoing description taken together with the appended claims constitute a disclosure such as to enable a person skilled in the marine engineering and oceanographic instrumentation arts and having the benefit of the teachings contained therein to make and use the invention. Further, the structure here described meets the aforestated objects of invention, and generally constitute a meritorious advance in the art unobvious to such a worker not having the benefit of these teachings.

What is claimed is:

1. An underwater port for an oceanographic submersible vehicle comprises:

transparent means having an interior and exterior surface and configured for mounting integrally in the hull of the oceanographic submersible vehicle for permitting light passage between the interior and exterior thereof;

first reflector means attached to said transparent means on the exterior surface thereof for changing the direction of light travel from transverse through the transparent means to parallel to the exterior surface thereof and vice-versa; and second reflector means attached to said transparent means on the exterior surface thereof and in optical alignment with said first reflector means to return light reflected by said first reflector means in a path approximately parallel to the direction of light travel exiting said reflector for transmission to the interior of the oceanographic submersible vehicle, whereby a transmission path is established adjacent said underwater port with a minimum of physical separation therefrom.

2. An underwater port according to claim 1 in which said first reflector means is attached to said transparent means by transparent cement having an index of refraction matching that of said transparent means.

3. An underwater port according to claim 1 in which said first reflector includes a first compound prism.

4. An underwater port according to claim 3 in which said first compound prism has a reflecting surface mounted at a critical angle to the light beam transmitted by the aforesaid transparent means and has exit and entrance faces at angles with respect to the underwater medium to eliminate reflection of the light beam thereat.

5. An underwater port according to claim 1 in which said second reflector means includes a second compound prism.

6. An underwater port according to claim 5 in which said second compound prism has two reflecting surfaces each at a critical angle with respect to the light path from said first to the exterior surface of the aforesaid transparent means and at converging angles with respect to each other and has entrance and exterior faces arranged at converging angles with respect to each other and at an angle to the entering and exiting light beam from said first reflector to minimize surface reflection thereat and two interior reflecting faces arranged at angles with respect to each other to intercept said light beam and provide total internal reflection thereof and to return said light beam to said first reflector.

7. An underwater port according to claim 2 in which said first reflector includes a first compound prism.

8. An underwater port according to claim 7 in which said first compound prism has a reflecting surface mounted at a critical angle to the light beam transmitted by the transparent means and has exit and entrance faces at angles with respect to the underwater medium to eliminate reflection of the light beam thereat.

9. An underwater port according to claim 7 in which said second reflector means includes a second compound prism.

10. An underwater port according to claim 9 in which said second compound prism has two exterior faces arranged at converging angles with respect to each other and at an angle to the entering and exiting light beam from said first reflector to minimize surface reflection thereat and two interior reflecting faces arranged at angles with respect to each other to intercept said light beam and provide total internal reflection thereof and to return said light beam to said first reflector.

* * * * *